US012765957B2

(12) United States Patent
Hares et al.

(10) Patent No.: US 12,765,957 B2
(45) Date of Patent: Oct. 20, 2026

(54) CONTROLLING MOVEMENT OF A SURGICAL ROBOT ARM

(71) Applicant: CMR SURGICAL LIMITED, Cambridge (GB)

(72) Inventors: Luke David Ronald Hares, Cambridge (GB); Paul Christopher Roberts, Cambridge (GB); Graham John Veitch, Cambridge (GB); Gordon Thomas Deane, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 3 days.

(21) Appl. No.: 19/177,728

(22) Filed: Apr. 14, 2025

(65) Prior Publication Data

US 2026/0157813 A1 Jun. 11, 2026

Related U.S. Application Data

(63) Continuation of application No. 18/383,104, filed on Oct. 24, 2023, now Pat. No. 12,295,685, which is a
(Continued)

(30) Foreign Application Priority Data

Feb. 25, 2020 (GB) ...................................... 2002643

(51) Int. Cl.
*A61B 34/35* (2016.01)
*A61B 34/00* (2016.01)
*A61B 34/30* (2016.01)

(52) U.S. Cl.
CPC .............. *A61B 34/35* (2016.02); *A61B 34/70* (2016.02); *A61B 34/74* (2016.02); *A61B 2034/301* (2016.02); *A61B 2034/305* (2016.02)

(58) Field of Classification Search
CPC ......... A61B 34/35; A61B 34/70; A61B 34/74; A61B 2034/301; A61B 2034/305; A61B 2034/742; A61B 34/30
(Continued)

(56) References Cited

U.S. PATENT DOCUMENTS 6,424,885 B1 * 7/2002 Niemeyer .............. A61B 34/77
600/109
6,459,926 B1 10/2002 Nowlin et al.
(Continued)

FOREIGN PATENT DOCUMENTS

JP 2012148379 A 8/2012
JP 2012157744 A 8/2012
(Continued)

OTHER PUBLICATIONS

Australian Notice of Acceptance for Patent Application from corresponding Australian Application No. 2021225384 dated Dec. 7, 2023.

(Continued)

*Primary Examiner* — Jaime Figueroa
(74) *Attorney, Agent, or Firm* — Lando & Anastasi, LLP

(57) ABSTRACT

A control system for a surgical robotic system, the surgical robotic system comprising a remote surgeon console and an articulated surgical robot arm comprising a series of joints extending from a base to a terminal end for attaching to an articulated surgical instrument. The control system comprises a central controller communicatively coupled to and remotely located from an arm controller of the surgical robot arm, the central controller also communicatively coupled to a surgeon input device of the surgeon console. The central controller is configured to: receive a command from the surgeon input device indicating a desired position of a distal end of the surgical instrument; transform the desired posi-
(Continued)

tion of the distal end to (i) a desired wrist position of a wrist of the surgical robot arm, and (ii) desired instrument drive joint positions for those joints of the surgical robot arm which drive joints of the articulated surgical instrument; and transmit the desired wrist position and desired instrument drive joint positions to the arm controller.

19 Claims, 8 Drawing Sheets

Related U.S. Application Data continuation of application No. 17/183,626, filed on Feb. 24, 2021, now Pat. No. 11,826,116.

(58) Field of Classification Search
USPC ................ 700/245–264; 318/568.11–568.25; 606/130
See application file for complete search history.

(56) References Cited

U.S. PATENT DOCUMENTS

| | | | | |
|---|---|---|---|---|
| 6,659,939 | B2 | 12/2003 | Moll et al. | |
| 6,699,177 | B1 * | 3/2004 | Wang | A61B 34/77 600/102 |
| 6,850,817 | B1 * | 2/2005 | Green | A61B 34/72 348/E13.016 |
| 7,107,124 | B2 * | 9/2006 | Green | A61B 34/72 700/262 |
| 7,789,875 | B2 * | 9/2010 | Brock | A61B 17/0469 606/1 |
| 7,865,266 | B2 | 1/2011 | Moll et al. | |
| 8,004,229 | B2 | 8/2011 | Nowlin et al. | |
| 8,262,560 | B2 * | 9/2012 | Whitman | A61B 1/00027 600/129 |
| 8,527,094 | B2 * | 9/2013 | Kumar | A61B 34/70 600/101 |
| 8,541,970 | B2 | 9/2013 | Nowlin et al. | |
| 8,600,551 | B2 | 12/2013 | Itkowitz et al. | |
| 8,620,473 | B2 | 12/2013 | Diolaiti et al. | |
| 8,749,190 | B2 * | 6/2014 | Nowlin | A61B 34/37 318/560 |
| 8,914,150 | B2 | 12/2014 | Moll et al. | |
| 8,918,211 | B2 | 12/2014 | Diolaiti et al. | |
| 8,945,095 | B2 * | 2/2015 | Blumenkranz | B25J 15/0009 606/1 |
| 9,002,518 | B2 | 4/2015 | Manzo et al. | |
| 9,014,856 | B2 | 4/2015 | Manzo et al. | |
| 9,107,683 | B2 | 8/2015 | Houtash et al. | |
| 9,271,798 | B2 | 3/2016 | Kumar et al. | |
| 9,333,042 | B2 | 5/2016 | Diolaiti et al. | |
| 9,510,911 | B2 * | 12/2016 | Hourtash | A61B 34/30 |
| 9,636,186 | B2 | 5/2017 | Kumar et al. | |
| 9,666,101 | B2 | 5/2017 | Kumar et al. | |
| 9,867,671 | B2 | 1/2018 | Kumar et al. | |
| 10,064,689 | B2 | 9/2018 | Swarup et al. | |
| 10,188,471 | B2 | 1/2019 | Brisson | |
| 10,510,267 | B2 | 12/2019 | Jarc et al. | |
| 10,610,316 | B2 | 4/2020 | Swarup et al. | |
| 10,617,480 | B2 | 4/2020 | Brisson | |
| 2002/0087049 | A1 * | 7/2002 | Brock | A61B 90/36 600/114 |
| 2002/0120252 | A1 | 8/2002 | Brock et al. | |
| 2002/0128633 | A1 | 9/2002 | Brock et al. | |
| 2002/0128661 | A1 * | 9/2002 | Brock | A61B 34/37 606/130 |
| 2003/0013949 | A1 | 1/2003 | Moll et al. | |
| 2005/0065658 | A1 * | 3/2005 | Green | A61B 17/00234 348/E13.016 |
| 2006/0142897 | A1 * | 6/2006 | Green | B25J 3/04 348/E13.016 |
| 2006/0178559 | A1 * | 8/2006 | Kumar | G16H 40/63 600/109 |
| 2007/0088340 | A1 | 4/2007 | Brock et al. | |
| 2007/0151390 | A1 * | 7/2007 | Blumenkranz | G01L 5/22 74/490.06 |
| 2008/0046122 | A1 | 2/2008 | Manzo et al. | |
| 2008/0125794 | A1 | 5/2008 | Brock et al. | |
| 2008/0177285 | A1 | 7/2008 | Brock et al. | |
| 2009/0088775 | A1 | 4/2009 | Swarup et al. | |
| 2010/0204713 | A1 | 8/2010 | Ruiz Morales | |
| 2010/0234857 | A1 | 9/2010 | Itkowitz et al. | |
| 2011/0264112 | A1 * | 10/2011 | Nowlin | A61B 34/77 606/130 |
| 2011/0276059 | A1 | 11/2011 | Nowlin et al. | |
| 2012/0191247 | A1 | 7/2012 | Kishi | |
| 2013/0110130 | A1 | 5/2013 | Manzo et al. | |
| 2013/0325029 | A1 * | 12/2013 | Hourtash | A61B 34/30 606/130 |
| 2013/0325030 | A1 * | 12/2013 | Hourtash | B25J 9/1676 606/130 |
| 2014/0052151 | A1 * | 2/2014 | Hingwe | A61B 34/30 606/130 |
| 2014/0052155 | A1 | 2/2014 | Hourtash et al. | |
| 2014/0276950 | A1 * | 9/2014 | Smaby | A61B 34/37 606/130 |
| 2014/0276951 | A1 | 9/2014 | Hourtash et al. | |
| 2014/0276953 | A1 | 9/2014 | Swarup et al. | |
| 2014/0276954 | A1 * | 9/2014 | Hourtash | A61B 34/37 606/130 |
| 2014/0316430 | A1 | 10/2014 | Hourtash | |
| 2014/0343569 | A1 | 11/2014 | Turner | |
| 2014/0358161 | A1 * | 12/2014 | Hourtash | B25J 9/1607 901/15 |
| 2017/0020614 | A1 | 1/2017 | Jackson et al. | |
| 2018/0214225 | A1 * | 8/2018 | Hourtash | B25J 18/007 |
| 2019/0183491 | A1 | 6/2019 | Shelton, IV et al. | |
| 2019/0231458 | A1 * | 8/2019 | DiMaio | A61B 17/34 |
| 2020/0367977 | A1 * | 11/2020 | Liu | A61B 34/30 |
| 2021/0259792 | A1 * | 8/2021 | Hares | A61B 34/30 |

FOREIGN PATENT DOCUMENTS

| | | | |
|---|---|---|---|
| JP | 2012171088 | A | 9/2012 |
| JP | 2016515405 | A | 5/2016 |
| JP | 2016518877 | A | 6/2016 |
| JP | 2018527200 | A | 9/2018 |
| JP | 2020510489 | A | 4/2020 |
| WO | 2018162921 | A1 | 9/2018 |
| WO | 2018216204 | A1 | 11/2018 |
| WO | 2019204013 | A1 | 10/2019 |

OTHER PUBLICATIONS

Chilean Resolution of Notification of Examiner's Report and Search Report from corresponding Chilean Application No. 202202318 dated Dec. 20, 2023.

Japanese Notification of Reasons for Refusal from corresponding Japanese Patent Application No. 2021-552229 dated Sep. 20, 2022.

Japanese Reconsideration Report by Eaminer before Appeal from corresponding Japanes Application No. 2021-552229 dated Dec. 7, 2023.

Notification of Transmittal of the International Search Report and the Written Opinion of the International Searching Authority from corresponding PCT/GB2021/050369 dated May 19, 2021.

United Kingdom Search Report from corresponding United Kingdom Application No. GB2002643.1 dated Jul. 22, 2020.

Russian Search Report from corresponding Russian Application No. 2023104417 dated Jun. 18, 2024.

* cited by examiner

CONTROLLING MOVEMENT OF A SURGICAL ROBOT ARM

CROSS-REFERENCE TO RELATED APPLICATION

This application is a continuation of U.S. patent application Ser. No. 18/383,104, filed Oct. 24, 2023, titled CONTROLLING MOVEMENT OF A SURGICAL ROBOT ARM, which is a continuation of U.S. patent application Ser. No. 17/183,626 [U.S. Pat. No. 11,826,116], filed Feb. 24, 2021, titled CONTROLLING MOVEMENT OF A SURGICAL ROBOT ARM, which claims the benefit under 35 U.S.C. § 119 of United Kingdom Patent Application No. 2002643.1 filed on Feb. 25, 2020. Each application referenced above is hereby incorporated herein by reference in its entirety for all purposes.

BACKGROUND

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articulated by means of multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. The surgical instrument comprises a shaft connected to a distal end effector 110 by a jointed articulation. The end effector engages in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot, where the corresponding joints are driven accordingly.

SUMMARY OF THE INVENTION

According to an aspect of the invention, there is provided a control system for a surgical robotic system, the surgical robotic system comprising a remote surgeon console and an articulated surgical robot arm comprising a series of joints extending from a base to a terminal end for attaching to an articulated surgical instrument, the control system comprising: a central controller communicatively coupled to and remotely located from an arm controller of the surgical robot arm, the central controller also communicatively coupled to a surgeon input device of the surgeon console, the central controller configured to: receive a command from the surgeon input device indicating a desired position of a distal end of the surgical instrument; transform the desired position of the distal end to (i) a desired wrist position of a wrist of the surgical robot arm, and (ii) desired instrument drive joint positions for those joints of the surgical robot arm which drive joints of the articulated surgical instrument; and transmit the desired wrist position and desired instrument drive joint positions to the arm controller.

The wrist of the surgical robot arm may be located on the surgical robot arm where the rotation axes of a set of distal joints of the surgical robot arm intersect and/or the rotation axes of joints of the articulated surgical instrument intersect, the set of distal joints of the surgical robot arm being located distal to the base.

The set of distal joints may consist of, in order, a roll joint, a pitch joint, a yaw joint, and a further roll joint.

The desired position of the articulated surgical instrument may comprise a location of the distal end and an orientation of the distal end.

The surgical instrument may be a surgical endoscope.

The surgical instrument may be configured to manipulate tissue, and the distal end of the surgical instrument may be an end effector.

The desired position of the articulated surgical instrument my further comprise a spread of two end effector elements of the end effector.

The instrument drive joints may be located proximal to the terminal end of the surgical robot arm.

The instrument drive joints may consist of three joints only.

The central controller may be configured to receive a virtual pivot point from the arm controller, the virtual pivot point being a position located in a port through which the surgical instrument passes at all times when inside a patient's body.

The central controller may be configured to receive an indication of the orientation of the surgical robot arm relative to the surrounding environment of the surgical robot arm from the arm controller.

The central controller may use the received virtual pivot point and the received indication of the orientation of the surgical robot arm to transform the desired position of the distal end to the desired wrist position and the desired instrument drive joint positions in the frame of reference of the surgical robot arm.

According to an aspect of the invention, there is provided an arm controller for a surgical robot arm, the surgical robot arm forming part of a surgical robotic system comprising a remote surgeon console, a central controller and the surgical robot arm, the surgical robot arm comprising a series of joints extending from a base to a terminal end for attaching to an articulated surgical instrument, the arm controller configured to: receive a desired wrist position of a wrist of the surgical robot arm, and desired instrument drive joint positions for those joints of the surgical robot arm which drive joints of the articulated surgical instrument; and for the remaining joints of the surgical robot arm, determine joint positions so as to cause the wrist of the surgical robot arm to adopt the desired wrist position, the remaining joints of the surgical robot arm being those which do not drive joints of the articulated surgical instrument; and send control signals to joint controllers of the surgical robot arm to drive the joints of the surgical robot arm to the desired instrument drive joint positions and the determined joint positions.

The wrist of the surgical robot arm may be located on the surgical robot arm where the rotation axes of a set of distal joints of the surgical robot arm intersect and/or the rotation axes of joints of the articulated surgical instrument intersect, the set of distal joints of the surgical robot arm being located distal to the base.

The set of distal joints may consist of, in order, a roll joint, a pitch joint, a yaw joint, and a further roll joint.

The remaining joints may comprise at least seven joints.

The remaining joints may comprise eight sequential joints.

The eight sequential joints may be, in order from the base, a roll joint, a pitch joint, a roll joint, a pitch joint, a roll joint, a pitch joint, a yaw joint and a roll joint.

The determined joint positions may be determined such that the surgical robot arm adopts an optimal configuration, the optimal configuration being so as to: (i) avoid any one joint of the remaining joints being proximal to a joint limit; and/or (ii) avoid the surgical robot arm being close to a joint singularity.

The arm controller may be configured to: determine a virtual pivot point, the virtual pivot point being located in a port through which the surgical instrument passes at all times when inside a patient's body; and transmit the virtual pivot point to the central controller.

The arm controller may be configured to transmit an indication of the orientation of the surgical robot arm relative to the surrounding environment of the surgical robot arm to the central controller.

According to an aspect of the invention, there is provided a surgical robotic system comprising: a surgical robot arm comprising: a series of joints extending from a base to a terminal end for attaching to an articulated surgical instrument; and an arm controller; a remote surgeon console comprising a surgeon input device; and a central controller communicatively coupled to the remote surgeon console and the arm controller of the surgical robot arm, the central controller configured to: receive a command from the surgeon input device indicating a desired position of a distal end of the surgical instrument; transform that desired position of the distal end to (i) a desired wrist position of a wrist of the surgical robot arm, and (ii) desired instrument drive joint positions for those joints of the surgical robot arm which drive joints of the articulated surgical instrument; transmit the desired wrist position and desired instrument drive joint positions to the arm controller; and the arm controller configured to: receive the desired wrist position and desired instrument drive joint positions; and for the remaining joints of the surgical robot arm, determine joint positions so as to cause the wrist of the surgical robot arm to adopt the desired wrist position, the remaining joints of the surgical robot arm being those which do not drive joints of the articulated surgical instrument; and drive the joints of the surgical robot arm to the received desired joint positions and the determined joint positions.

BRIEF DESCRIPTION OF THE FIGURES

The present invention will now be described by way of example with reference to the accompanying drawings. In the drawings.

DETAILED DESCRIPTION

Figure 1:
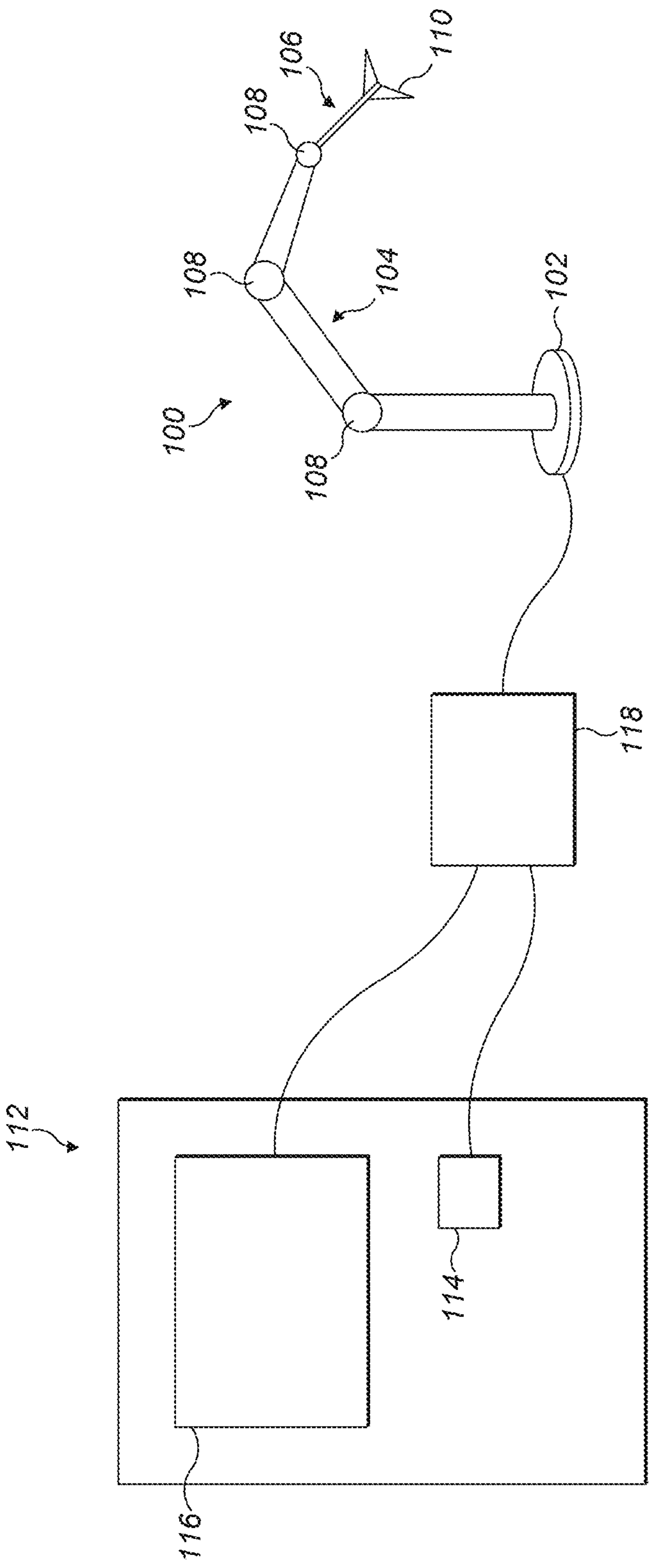
FIG. 1 illustrates a surgical robotic system for performing a surgical procedure.

The following describes controlling a surgical robot arm and an attached surgical instrument. The control system is distributed, having an arm controller co-located with the surgical robot arm, and a central controller located remotely from the surgical robot arm. The surgical robot arm and surgical instrument form part of a surgical robotic system, along with a remote surgeon console, of the type illustrated in FIG. 1. The surgical robotic system may comprise more than one surgical robot arm, each having an attached surgical instrument and a co-located arm controller.

The control system and methods described in the following are done so with respect to a surgical robot arm holding a surgical instrument having an end effector at its distal end for manipulating tissue of the patient at the surgical site. The end effector may be, for example, a pair of jaws, scalpel, suturing needle etc. However, the same surgical robot arm, control system and methods apply equally to a surgical instrument which is an endoscope having a camera at its distal end for capturing a video feed of the surgical site.

Figure 2:
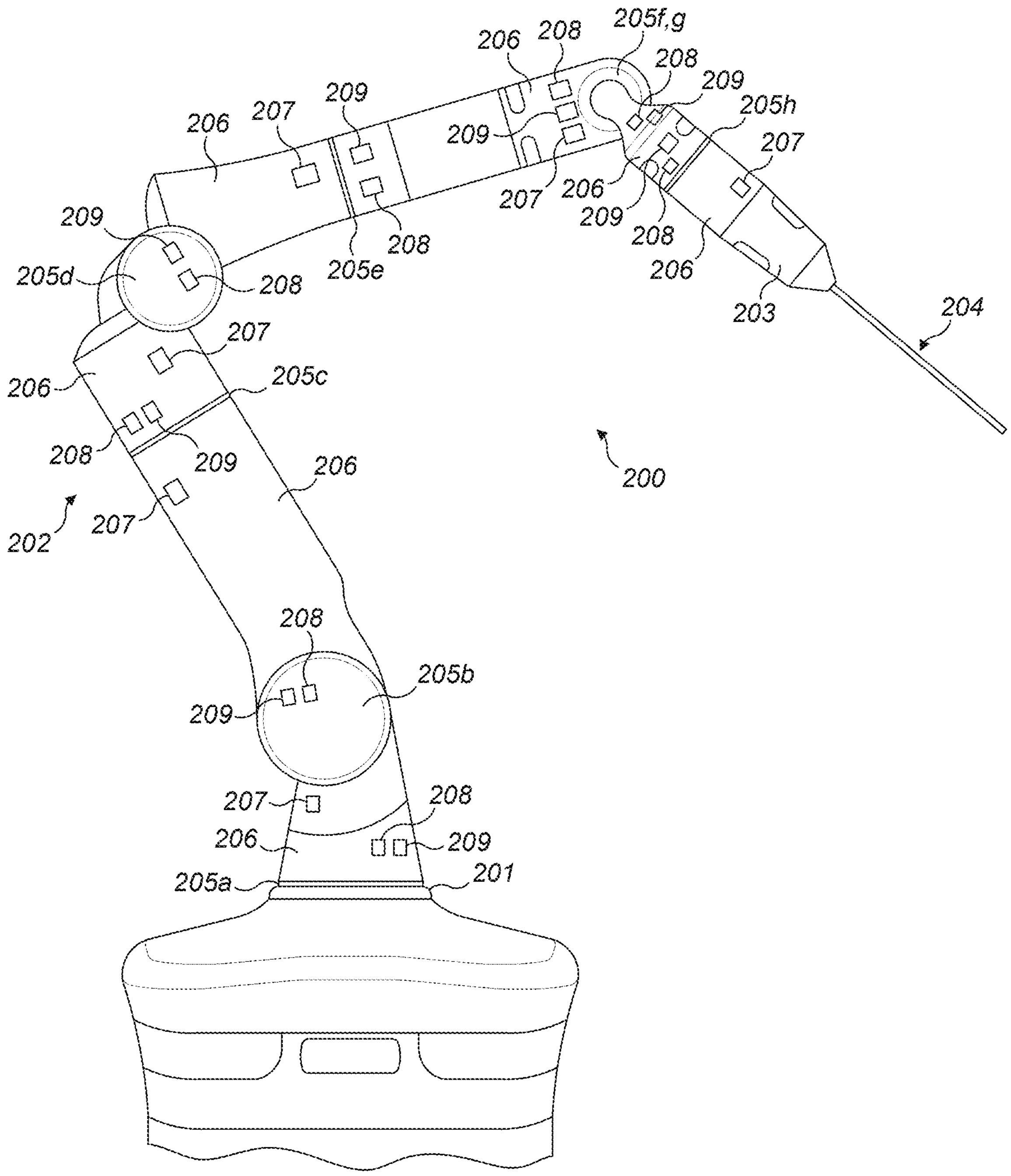
FIG. 2 illustrates a surgical robot.

FIG. 2 illustrates an exemplary surgical robot 200. The robot comprises a base 201 which is fixed in place when a surgical procedure is being performed. Suitably, the base 201 is mounted to a chassis. In FIG. 2, the chassis is a cart. This cart may be a bedside cart for mounting the robot at bed height. Alternatively, the chassis may be a ceiling mounted device, or a bed mounted device.

A robot arm 202 extends from the base 201 of the robot to a terminal end 203 for attaching to a surgical instrument 204. The arm is flexible. It is articulated by means of multiple flexible joints 205 along its length. In between the joints are rigid arm links 206. Suitably, the joints are revolute joints. The robot arm has at least seven joints between the base and the terminal end. The robot arm 200 illustrated in FIG. 2 has eight joints in total between the base 201 and the terminal end 203. The robot arm illustrated in FIG. 2 has only eight joints between the base and the terminal end. The joints include one or more roll joints (which have an axis of rotation along the longitudinal direction of the arm links on either side of the joint), one or more pitch joints (which have an axis of rotation transverse to the longitudinal direction of the preceding arm link), and one or more yaw joints (which also have an axis of rotation transverse to the longitudinal direction of the preceding arm link and also transverse to the rotation axis of a co-located pitch joint). In the example of FIG. 2: joints 205*a*, 205*c*, 205*e* and 205*h* are roll joints; joints 205*b*, 205*d* and 205*f* are pitch joints; and joint 205*g* is a yaw joint. The order of the joints sequentially from the base 201 of the robot arm to the terminal end 203 of the robot arm is: roll, pitch, roll, pitch, roll, pitch, yaw, roll. There are no intervening joints in FIG. 2.

Figure 3:
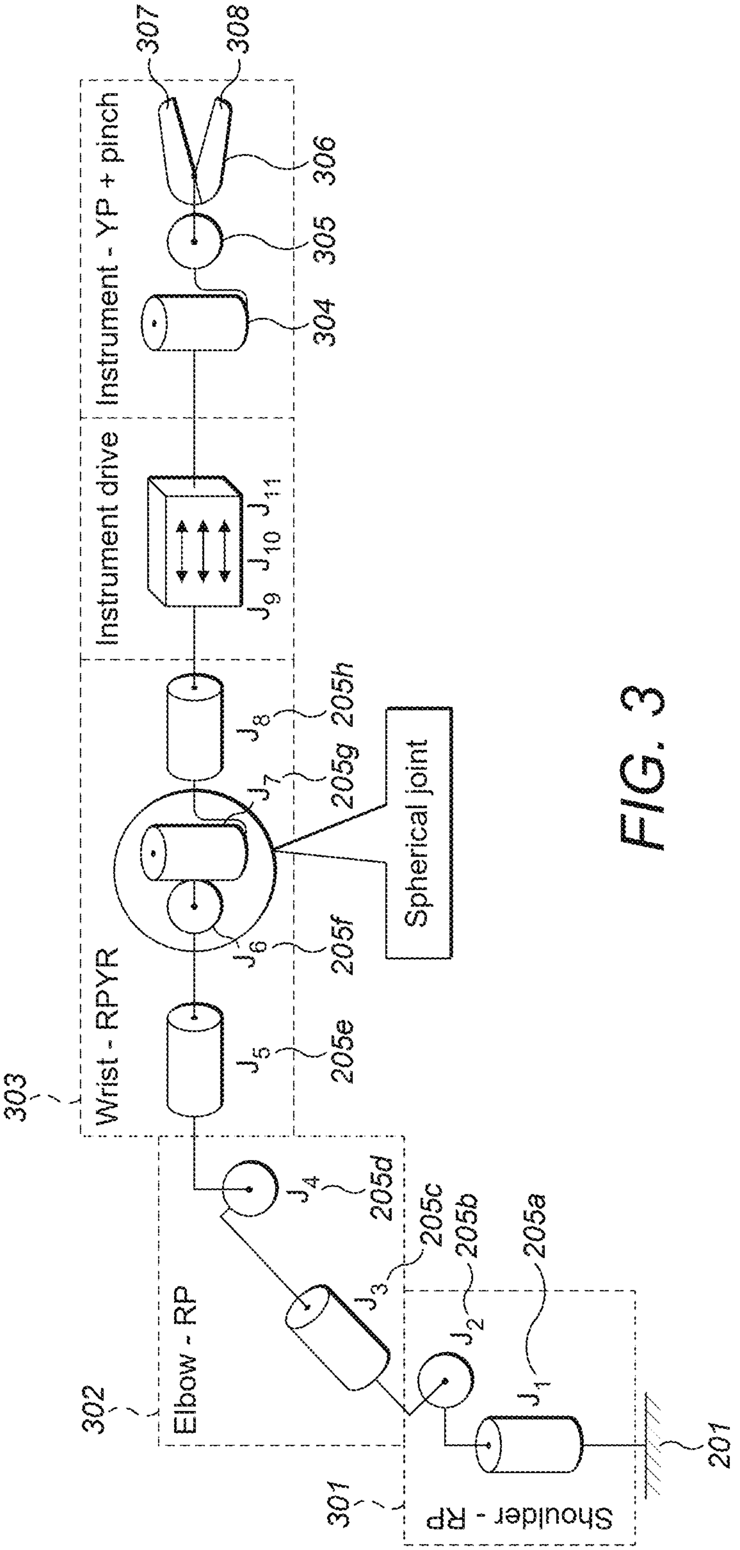
FIG. 3 illustrates an exploded view of the joints of the surgical robot arm of FIG. 2.

The joints of the surgical robot arm of FIG. 2 are illustrated on FIG. 3. The robot arm is articulated by a shoulder portion 301, elbow portion 302, and wrist portion 303. The shoulder portion 301 is adjacent to the base 201 and consists of a roll joint $J_1$ 205*a* adjacent to the base 201 followed by a pitch joint $J_2$ 205*b*. The pitch joint $J_2$ has a rotation axis perpendicular to the rotation axis of the roll joint $J_1$. The elbow portion 302 is between the shoulder portion 301 and the wrist portion 303. The elbow portion

302 consists of: a roll joint $J_3$ 205*c* adjacent to the pitch joint $J_2$ of the shoulder portion 301, followed by a pitch joint $J_4$ 205*d*. The pitch joint $J_4$ has a rotation axis perpendicular to the rotation axis of the roll joint $J_3$. The wrist portion 303 is adjacent to the elbow portion 302. The wrist portion 303 consists of a roll joint $J_5$ 205*e* adjacent to the pitch joint $J_4$ of the elbow portion 302, followed by a pitch joint $J_6$ 205*f* and a yaw joint $J_7$ 205*g*, followed by a roll joint $J_8$ 205*h*. The pitch joint $J_6$ and yaw joint $J_7$ form a compound joint, which may be a spherical joint, as illustrated on FIG. 3. The pitch joint $J_6$ and the yaw joint $J_7$ have intersecting axes of rotation.

The end of the robot arm distal to the base can be articulated relative to the base by movement of one or more of the joints of the arm. The rotation axes of the set of distal joints $J_5$, $J_6$, $J_7$ and $J_8$ in the wrist portion 303 all intersect at a point on the surgical robot arm. The description herein refers to a wrist. Suitably, the wrist is a portion of the robot arm which rigidly couples to the distal end of an instrument when that instrument is attached to the robot arm. The wrist has a position and an orientation. For example, the position of the wrist may be the intersection of the rotation axes of $J_5$, $J_6$, $J_7$ and $J_8$. Alternatively, the position of the wrist may be the intersection of one or more rotation axes of joints of the instrument. Alternatively, the position of the wrist may be the intersection of one or more rotation axes of the distal joints of the robot arm and one or more rotation axes of joints of the instrument. The surgical robot arm illustrated in FIGS. 2 and 3 has a redundant joint. For a given position of the wrist relative to the base of the surgical robot arm, there is more than one configuration of the joints $J_1$ to $J_4$.

Thus, the surgical robot arm can adopt different poses whilst maintaining the same wrist position.

The surgical robot arm could be jointed differently to that illustrated in FIGS. 2 and 3. For example, the arm may have fewer than eight or more than eight joints. The arm may include joints that permit motion other than rotation between respective sides of the joint, for example a telescopic joint.

Returning to FIG. 2, the surgical robot arm comprises a set of motors 207. Each motor 207 drives one or more of the joints 205. Each motor 207 is controlled by a joint controller. The joint controller may be co-located with the motor 207. A joint controller may control one or more of the motors 207. The robot arm comprises a series of sensors 208, 209. These sensors comprise, for each joint, a position sensor 208 for sensing the position of the joint, and a torque sensor 209 for sensing the applied torque about the joint's rotation axis. One or both of the position and torque sensors for a joint may be integrated with the motor for that joint. The outputs of the sensors are passed to the control system.

The surgical instrument 204 attaches to a drive assembly at the terminal end of the robot arm 203. This attachment point is at all times external to the patient. The surgical instrument 204 has an elongate profile, with a shaft spanning between its proximal end which attaches to the robot arm and its distal end which accesses the surgical site within the patient body. The surgical instrument may be configured to extend linearly parallel with the rotation axis of the joint 205*h* of the arm. For example, the surgical instrument may extend along an axis coincident with the rotation axis of the joint 205*h* of the arm.

The proximal end of the surgical instrument and the instrument shaft may be rigid with respect to each other and rigid with respect to the distal end of the robot arm when attached to it. An incision is made into the patient body, through which a port is inserted. The surgical instrument may penetrate the patient body through the port to access the surgical site. Alternatively, the surgical instrument may penetrate the body through a natural orifice of the body to access the surgical site. At the proximal end of the instrument, the shaft is connected to an instrument interface. The instrument interface engages with the drive assembly at the distal end of the robot arm. Specifically, individual instrument interface elements of the instrument interface each engage a respective individual drive assembly interface element of the drive assembly. The instrument interface is releasably engageable with the drive assembly. The instrument can be detached from the robot arm manually without requiring any tools. This enables the instrument to be detached from the drive assembly quickly and another instrument attached during an operation.

At the distal end of the surgical instrument, the distal end of the instrument shaft is connected to an end effector by an articulated coupling. The end effector engages in a surgical procedure at the surgical site. The end effector may be, for example, a pair of jaws, a pair of monopolar scissors, a needle holder, a fenestrated grasper, or a scalpel. The articulated coupling comprises several joints. These joints enable the pose of the end effector to be altered relative to the direction of the instrument shaft. The end effector itself may also comprise joints. The end effector illustrated in FIGS. 2 and 3 has a pair of opposing end effector elements 307, 308. The joints of the end effector are illustrated on FIG. 3 as a pitch joint 304, a yaw joint 305 and a pinch joint 306. The pitch joint 304 is adjacent to the shaft of the instrument and rotates about an axis perpendicular to the longitudinal axis of the instrument shaft. The yaw joint 305 has a rotation axis perpendicular to the rotation axis of the pitch joint 304. The pinch joint 306 determines the spread of the end effector elements. In practice, the pinch joint 306 may be another yaw joint which has the same rotation axis as the yaw joint 305. Independent operation of the two yaw joints 305, 306 can cause the end effector elements to yaw in unison, and/or to open and close with respect to each other.

Drive is transmitted from the robot arm to the end effector in any suitable manner. For example, the joints of the instrument may be driven by driving elements such as cables, push rods or push/pull rods. These driving elements engage the instrument interface at the proximal end of the instrument. The drive assembly at the terminal end of the robot arm comprises instrument drive joints which transfer drive from the surgical robot arm to the instrument interface via the respective interface elements described above, and thereby to the instrument joints. These instrument drive joints are shown on FIG. 3 as joints $J_9$, $J_{10}$ and $J_{11}$. FIG. 3 illustrates three instrument drive joints, each one of which drives one of the three joints of the instrument.

Suitably, the instrument drive joints are the only means by which drive is transferred to the instrument joints. The robot arm may have more or fewer than three instrument drive joints. The surgical instrument may have more or fewer than three joints. The instrument drive joints may have a one-to-one mapping to the instrument joints that they drive, as shown in FIG. 3. Alternatively, an instrument drive joint may drive more than one instrument joint.

The surgeon console is located remotely from the one or more surgical robot arms of the surgical robotic system. The surgeon console comprises one or more surgeon input devices and a display. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate.

Figure 4:
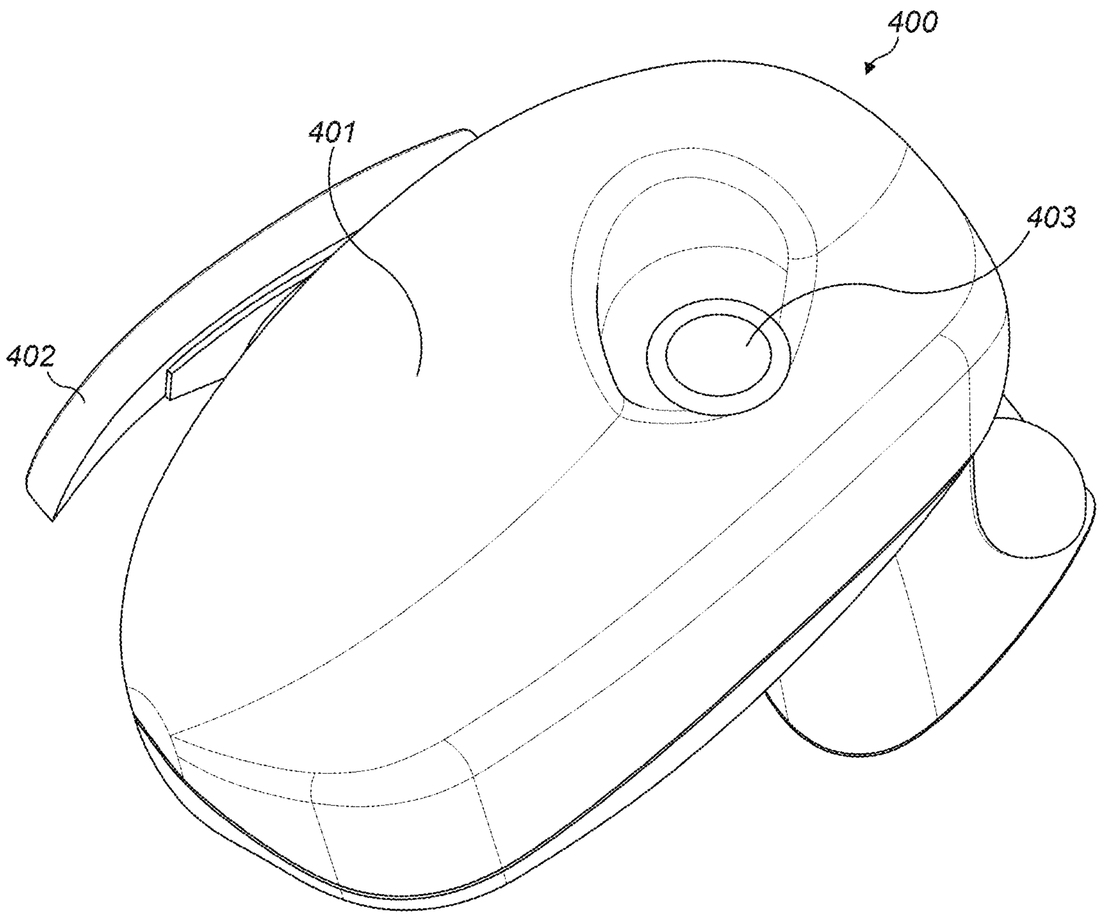
FIG. 4 illustrates an exemplary hand controller of a surgeon console.

FIG. 4 illustrates an exemplary hand controller 400. The hand controller is connected to the surgeon console, for example by a gimbal arrangement (not shown). This enables the hand controller to be moved with three degrees of translational freedom with respect to the surgeon console. Such movement may be used to command corresponding movement of the end effector of the instrument. The hand controller may also be rotated with respect to the surgeon console. Such movement may be used to command corresponding rotation of the end effector of the instrument.

The hand controller shown is intended to be held by a right hand. A mirror image hand controller could be held by a left hand. The hand controller comprises a body 401 suitable for being gripped by a hand. The hand controller may comprise additional inputs, for example buttons, switches, levers, slide inputs or capacitive sensor inputs such as track pads 403. The hand controller of FIG. 4 comprises a trigger 402. The trigger 402 is movable relative to the body 401. In the hand controller shown, the trigger 402 is rotatable relative to the body 401. Alternatively, or in addition, the trigger could translate linearly relative to the body 401. Movement of the trigger 402 relative to the body 401 may be used to command opening and closing of the end effector elements of the instrument. The hand controller may comprise two triggers, each trigger for independently controlling a single different one of the end effector elements.

The surgeon console may comprise two or more surgeon input devices. Each surgeon input device may be used to control a different surgical instrument. Thus, a surgeon may control one surgical instrument using a hand controller in his left hand, and control another surgical instrument using a hand controller in his right hand.

Figure 5:
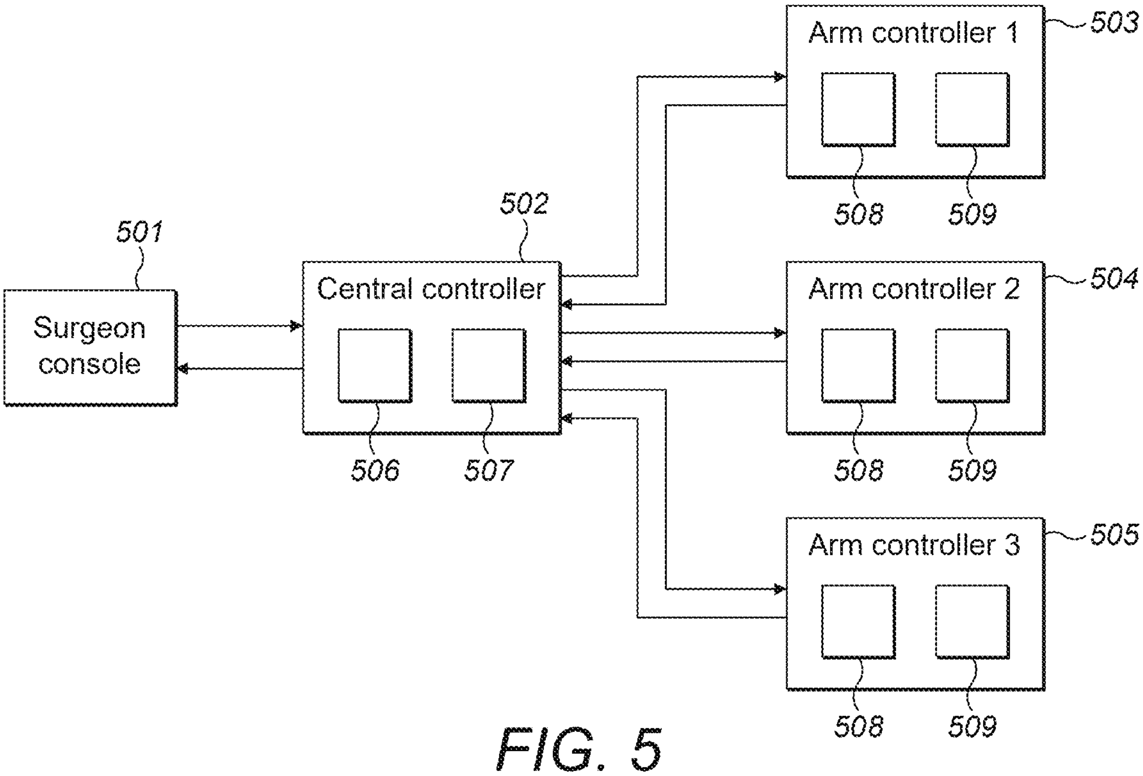
FIG. 5 is a schematic diagram illustrating the control system of a surgical robotic system.

A control system connects the surgeon console to the one or more surgical robots. Such a control system is illustrated in FIG. 5. The surgeon console 501 is connected by a bi-directional communications link to a central controller 502. Specifically, the surgeon input device(s) of the surgeon console 501 are communicatively coupled to the central controller 502. The central controller 502 is connected by a bi-directional communications link to an arm controller 503, 504, 505 of each surgical robot arm of the surgical robotic system. Each arm controller is co-located with a surgical robot arm. The arm controller may be located in the chassis which supports the surgical robot arm, for example in the cart of the arm. The central controller is remotely located from at least one of the surgical robot arms. Suitably, the central controller is remotely located from all the surgical robot arms in the surgical robotic system. The central controller may be located at the surgeon console. Alternatively, the central controller may be co-located with one of the arm controllers. The central controller may be located remote from both the surgeon console and all the arm controllers.

The central controller comprises a processor 506 and a memory 507. The memory 507 stores, in a non-transient way, software code that can be executed by the processor 506 to cause the processor to control the surgeon console and the one or more surgical robot arms and instruments in the manner described herein.

Each of the arm controllers comprises a processor 508 and a memory 509. The memory 509 stores, in a non-transient way, software code that can be executed by the processor 508 to cause the processor to control the surgeon console and the one or more surgical robot arms and instruments in the manner described herein.

The central controller 502 receives commands from the surgeon input device(s). The commands from one surgeon input device indicate a desired position of a distal end of a surgical instrument. The desired position of the distal end of the surgical instrument comprises the location of the end effector. The desired position of the distal end may also comprise the orientation of the distal end. The desired position of the distal end may also, or alternatively, comprise a spread of two opposing end effector elements of an end effector. The commands from the surgeon input device may indicate a desired absolute location and/or orientation and/or spread of the end effector. Alternatively, the commands from the surgeon input device may indicate a desired change in the absolute location and/or orientation and/or spread of the end effector.

The control system converts the commands received from the surgeon input device to drive signals to drive joint(s) of its associated surgical robot arm and/or surgical instrument. The joints are thereby driven to cause the distal end to adopt the desired position commanded by the surgeon input device. Manipulation of the surgical instrument is thereby controlled by the control system in response to manipulation of the surgeon input device.

The processing of the commands received from the surgeon input device to drive signals for driving joints of a surgical robot arm is distributed between the central controller 502 and the arm controller 503 of that surgical robot arm. As described in more detail below, the central controller 502 determines the wrist position of the surgical robot arm and the instrument drive joint positions. It passes these to the arm controller. The arm controller then determines the joint positions of the remaining joints to achieve the desired wrist position. The arm controller sends commands to the joint controllers distributed in the arm. The joint controllers then control the joint motors to drive the joints of the arm to move to the determined joint positions.

Figure 6:
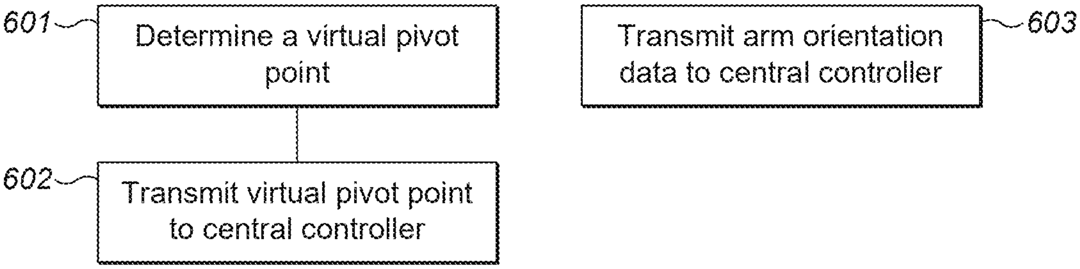
FIG. 6 is a flowchart illustrating a control method of an arm controller.

FIG. 6 is a flowchart showing steps which may be carried out by an arm controller during a set up mode of its surgical robot arm. At step 601, the arm controller determines a virtual pivot point of the surgical instrument in the patient's body. The virtual pivot point is the natural centre of rotation of an instrument having a rigid shaft as that instrument moves in the patient's body. A port is inserted into the abdominal wall of the patient. The port is of the order of 2-10 cm long. The instrument is inserted into the patient's body through the port. The virtual pivot point lies along the length of the port. The exact location of the virtual pivot point depends on the patient's anatomy, and hence differs from patient to patient. The virtual pivot point can be determined using the following method.

With the instrument located in the port, an operator moves the distal end of the robot arm in directions generally transverse to the instrument shaft. This motion causes the port to exert a lateral force on the instrument shaft where it passes through the port, with the result that the instrument applies a torque to the joints of the arm—in this case joints $J_6$ **205*f* and $J_7$ 205*g*—whose axes are transverse to the longitudinal axis of the instrument shaft. The position of each arm joint is measured by its associated position sensor 208, and this sensed position is output to the arm controller. The torque at each arm joint is measured by its associated torque sensor 209**, and this sensed torque is output to the arm controller. Thus, as the operator moves the distal end of the robot arm laterally the arm controller receives sensed inputs indicating the position and forces on the arm joints. That information allows the controller to estimate: (a) the position of the distal end of the robot relative to the fixed base and (b) the vector of the instrument shaft relative to the distal end of the robot. Since the instrument shaft passes through the passageway of the port, the passageway of the port must lie along that vector. As the distal end of the robot arm is moved, the controller calculates multiple pairs of distal end positions and instrument shaft vectors. Those vectors all converge, from their respective distal end position, on the location of the virtual pivot point in the passageway of the port. By collecting a series of those data pairs and then solving for the mean location where the instrument shaft vectors converge, the arm controller determines the virtual pivot point relative to the base.

Having determined the virtual pivot point in the robot arm's frame of reference, i.e. relative to the fixed base of the robot arm, the arm controller transmits that virtual pivot point to the central controller at step 602. Whilst the base of the robot remains in the same fixed position, and the patient remains in the same position relative to the base of the robot, the natural centre of rotation of the instrument in the patient's body remains the same. Thus, the arm controller may determine the virtual pivot point in a calibration mode during set-up of the robot arm prior to a surgical procedure taking place, and transmit the virtual pivot point to the central controller only once at this time. Alternatively, the arm controller may continually or periodically re-calculate the virtual pivot point during a surgical procedure from the sensory data passed to the arm controller from sensors as the robot arm is moved during surgery. Those sensors may be any one or combination of: sensors on the robot arm such as sensors 208 and 209; and sensors external to the robot arm, such as sensors on the instrument and/or the port. Sensors external to the robot arm may send sensory data wirelessly to the arm controller. The arm controller may then continually or periodically transmit the re-calculated virtual pivot point to the central controller during the surgical procedure. A reason to re-calculate the virtual pivot point regularly is that although the base of the robot arm remains fixed during a surgical procedure, the position of the patient relative to the base of the robot arm may change due to movement of the patient on the bed, for example as a result of breathing, and hence the natural centre of rotation of the instrument may shift over time. If the base of the robot arm is moved, for example if the instrument is removed from the body, and the cart on which the robot arm is mounted is wheeled to a different position at the patient's bedside, then the method above is reperformed in order to work out the new virtual pivot point.

At step 603, the arm controller may, optionally, transmit arm orientation data to the central controller. If the surgical robotic system has two or more robot arms, then it is useful for the control system to assess the robot arms in the same frame of reference. For example, for the purpose of avoiding collisions between those robot arms as they move. Or for the purpose of mapping left and right directions in the hand controllers' reference frame, and left and right end effector movements as shown in the video feed from the endoscope.

Figure 7:
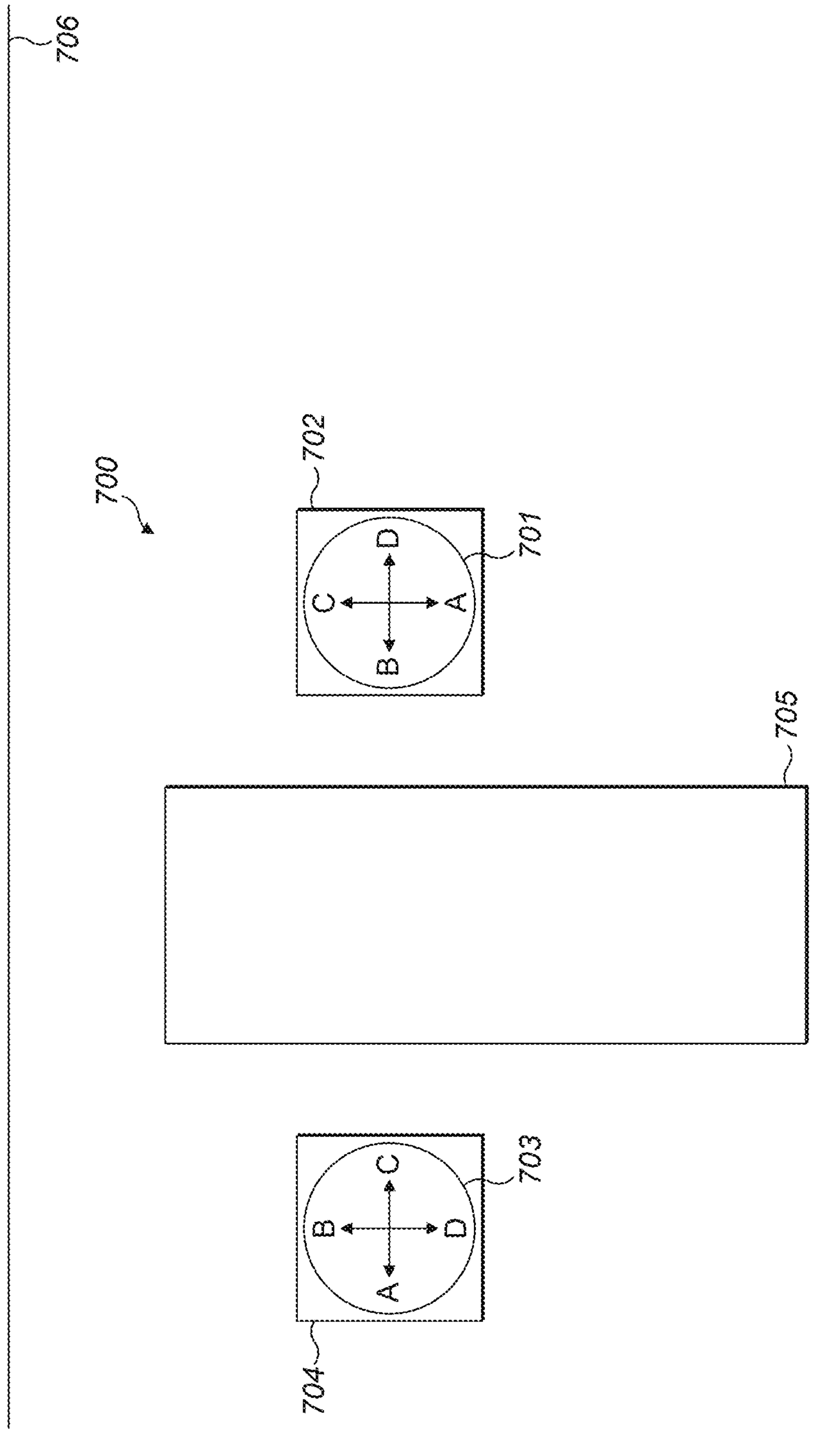
FIG. 7 is a schematic diagram illustrating orientation interfaces of two surgical robot arms.

The robot arm base, or the chassis on which the robot arm is fixed, may have an orientation interface which an operator can manipulate to identify an orientation of the robot arm relative to the surrounding environment of the robot arm. FIG. 7 illustrates the orientation interface 701 of robot arm 702, and the orientation interface 703 of robot arm 704. The robot arms 702 and 704 are located on opposing sides of patient bed 705. The orientation interface may be, for example, a button or set of buttons accessible to an operator, such as a member of the bedside team. Each orientation interface may comprise four buttons, each button indicating one of four directions, as shown in FIG. 7. These four directions are equally spaced, with 90° between each direction, i.e. at 0°, 90°, 180° and 270°. Alternatively, any number of directions may be indicated. For example, the interface may comprise a dial which can be rotated by the operator in increments of 1°. The operator may provide an input to the orientation interface of each robot arm in order to identify the orientation of each robot arm relative to the surrounding environment. As an example, the operator may identify a common direction from each of the robot arms. For example, the operator may identify the direction of the wall 706 of the operating theatre by actuating the buttons facing the wall 706 on each robot arm. In the case of FIG. 7, this would be by actuating button C on orientation interface 701, and actuating button B on orientation interface 703. As another example, the operator may identify the direction of the robot arm holding the endoscope by actuating the buttons on each robot arm. The arm controller receives the input indicating the orientation of the surgical robot arm relative to the surrounding environment from the orientation interface, and transmits this indication to the central controller.

Step 603 is optional. Orientation data may be acquired by the central controller by other means. For example, it may be the case that the relative orientation of the surgical robot arms is known by virtue of those robot arms being positioned in predetermined orientations, for example if they are attached to the patient's bed in predetermined orientations.

Figure 8:
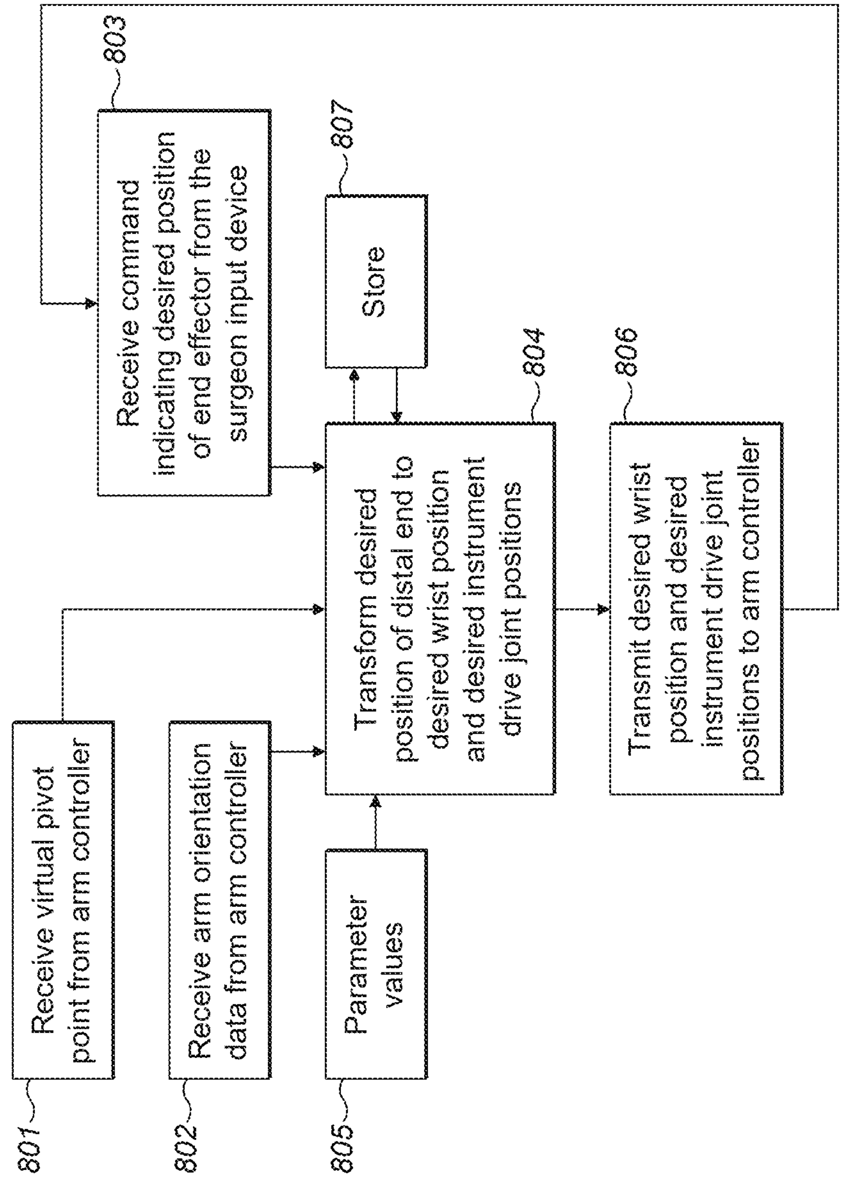
FIG. 8 is a flowchart illustrating a control method of a central controller.

FIG. 8 is a flowchart showing steps which may be carried out by the central controller during operation of a surgical robot arm. At step 801, the central controller receives the virtual pivot point from the arm controller. At step 802, the central controller may (optionally) receive orientation data from the arm controller. At step 803, the central controller receives a command from the surgeon input device(s) indicating a desired position of the distal end of the surgical instrument. As described above, this desired position may include a desired location and/or an orientation and/or spread of the end effector.

At step 804, the central controller transforms the desired position of the distal end to a desired wrist position and desired instrument drive joint positions as follows.

The virtual pivot point received from the arm controller is in the frame of reference of the robot arm, i.e. relative to the robot arm base. The central controller rotates the virtual pivot point from the robot arm frame of reference to a common ground frame of reference using orientation data. This orientation data may be that received from the arm controller as described above. Alternatively, the orientation data may be predetermined, as described above, and retrieved from a parameter value store of the central controller.

FIG. 8 illustrates a control loop. In each iteration of the control loop, the central controller receives a command from the surgeon input device indicating a desired position of the distal end of the surgical instrument. The central controller uses the command to update one or more parameters of the robot arm that it calculated in the previous iteration of the control loop. All or a subset of the parameters which are updated are stored in store 807, and then retrieved from store 807 in the next iteration of the control loop. These parameters may include the desired position of the distal end in the common ground frame of reference, the desired wrist position, and the desired instrument drive joint positions.

The desired wrist position comprises the location of the wrist. The desired wrist position may also comprise the orientation of the wrist.

In order to determine the desired wrist position and desired instrument drive joint positions at step 804, the central controller may first determine a desired position of the distal end of the instrument relative to a common ground frame of reference using the command from the surgeon input device. Suitably, the central controller does this by retrieving the last desired position of the distal end relative to a common ground frame of reference from the store 807. That last desired position of the distal end relative to the common ground frame of reference is then updated using the command from the surgeon input device. For example, with the hand controller of FIG. 4, the central controller may transform a detected translation of the hand controller to a translation of the end effector, a detected rotation of the hand controller to a rotation of the end effector, and a detected angle of the trigger of the hand controller to a spread angle of end effector elements of the end effector.

The central controller may use parameter values stored in memory when updating the desired position of the distal end of the surgical instrument using the commands received from the surgeon input device. For example, the central controller may use a stored parameter value identifying the current endoscope position as received from position sensory data received by the central controller from the arm controller of the robot arm holding the endoscope. The surgeon manipulates the surgeon input device responsive to the view from the endoscope as seen on the console display. Thus, the central controller rotates and/or translates the movement commanded by the surgeon's manipulation of the surgeon input device in order to account for the viewing direction of the end effector as seen by the surgeon. More specifically, the central controller uses the relative orientation between the endoscope orientation and the surgical instrument orientation to determine the rotation between the hand controller movements and the end effector movements.

The central controller may use a stored parameter value identifying the mapping between the surgeon input device and the distal end of the surgical instrument. For example, the central controller may have stored parameters identifying one or more of the following: the ratio between translational movement of the surgeon's hand controller and translational movement of the end effector; the ratio between rotational movement of the surgeon's hand controller and rotational movement of the end effector; and a relationship mapping the position of the trigger to an angular spread of the end effector elements. The central controller applies these mappings when transforming the inputs from the surgeon input device to an updated desired position of the distal end of the surgical instrument.

The central controller may use a clutch model when updating the desired position of the end effector. A clutch mode is used to allow the surgeon input device to be repositioned. This may be desired if the surgeon input device is in an ergonomically poor position, or if the surgeon input device has reached a limit in a range of motion. When the surgeon engages a clutch mode the surgeon input device is disengaged from controlling the surgical robot arm. Movement of the surgeon input device during an engaged clutch mode is not converted to movement of the end effector. When the surgeon disengages the clutch mode, the surgeon input device re-engages control of the surgical robot arm. The central controller responds to use of the clutch by synchronising the first commanded end effector position received from the surgeon input device following re-engagement with the current end effector position. Thus, if the surgeon input device has been translated or rotated across the surgeon input device's workspace whilst clutched, it does not result in a sudden movement of the end effector to adopt the change in position of the surgeon input device from when the clutch mode was engaged to when it was disengaged.

The central controller may use a synchronisation model when updating the desired position of the end effector. A synchronisation model is used to account for when a joint of the surgical robot arm or instrument reaches a joint limit, or when the wrist is too close to the virtual pivot point. The synchronisation model is similar to the clutch model in that the central controller responds to use of the synchronisation function by synchronising the first commanded end effector position received from the surgeon input device following use of the synchronisation model with the current end effector position.

Once the central controller has determined a desired position of the distal end of the surgical instrument relative to a common ground frame of reference using the command from the surgeon input device and one or more of the parameters described above, the central controller rotates the desired position of the distal end of the surgical instrument from the common ground frame of reference to the robot arm frame of reference.

Next the central controller uses inverse kinematics to determine the instrument drive joint positions and wrist position to achieve the desired position of the distal end of the surgical instrument in the robot arm frame of reference. Any appropriate Inverse kinematics equations known in the art may be used.

The location of the wrist of the surgical robot arm is fixed relative to the location of the distal end of the surgical instrument in the robot arm frame of reference. The instrument is rigid, and the location of the wrist (as defined above) is a point which lies on the longitudinal axis of the instrument shaft. The distance between the distal end of the surgical instrument and the location of the wrist is known: it is the length of the arm between the wrist and the arm's terminal end plus the length of the instrument minus any overlapping portion of the arm and instrument. The instrument shaft at all times passes through the virtual pivot point when the instrument is inside the patient's body. Since the virtual pivot point is known, for a given distal end of the surgical instrument position there is a unique wrist location. Thus, there is a one-to-one relationship between the distal end location and the wrist location. Thus, the central controller determines the desired wrist location in the robot arm's frame of reference from the desired location of the distal end in the robot arm's frame of reference, the known virtual pivot point, and the known distance between the location of the distal end and the wrist.

The central controller converts the determined rotation of the end effector and the determined spread of the end effector elements to desired instrument drive joint positions. To do this, the central controller uses a stored mapping between the movement of each joint of the instrument and the movement of the robot arm's instrument drive joint(s) driving that instrument joint. This mapping may be altered during calibration of the drive assembly prior to, or during, an operative procedure. For the exemplary robot of FIG. 3, the central controller determines three instrument drive joint positions.

At step 806, the central controller transmits the desired wrist position and the desired instrument drive joint positions to the arm controller.

The control loop then returns to step 803, where the central controller receives the next command from the surgeon input device.

Figure 9:
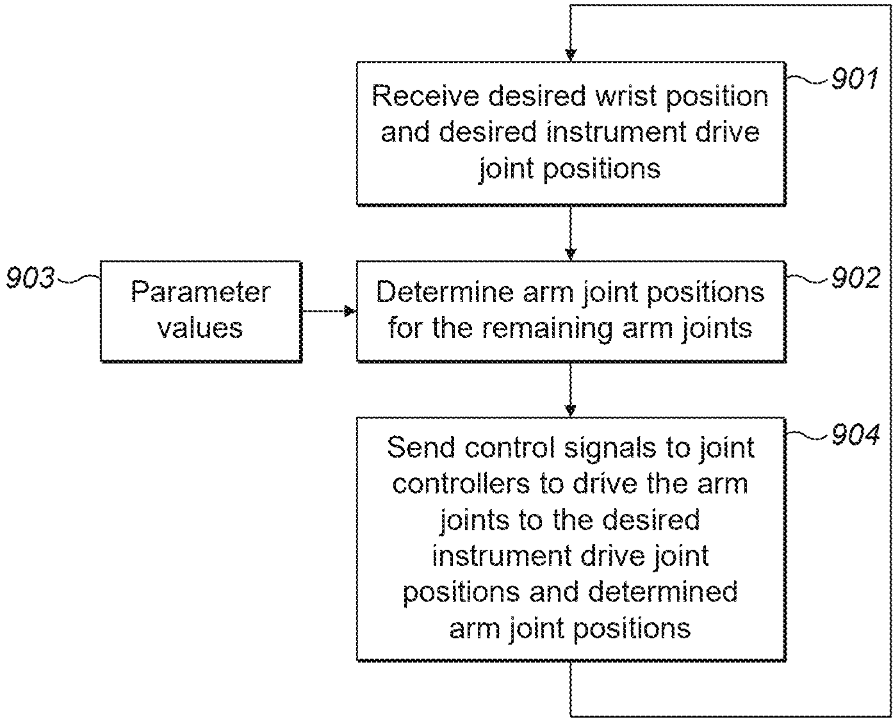
FIG. 9 is a flowchart illustrating a control method of an arm controller.

FIG. 9 illustrates a control loop which is implemented by the arm controller to control the surgical robot arm to move as commanded by the surgeon input device. At step 901, the arm controller receives the desired wrist position and the desired instrument drive joint positions from the central controller.

At step 902, the arm controller determines joint positions of the remaining joints of the robot arm which do not drive joints of the instrument, i.e. joints $J_1$ to $J_8$ inclusive. The determined joint positions are such that the wrist has the desired position received from the central controller. Given the known fixed base position and the desired wrist position, the arm controller uses an inverse kinematics method to determine the joint positions for the remaining joints of the arm $J_1$ to $J_8$. Any suitable inverse kinematics method known in the art may be used. The arm controller uses known parameter values 903 to determine the joint positions. Those known parameter values include: the known structure of the robot arm; the known dimensions and masses of each link and joint of the robot arm; the known dimensions and mass of the attached surgical instrument; and the inertias of the joints. The inertias of the joints are calculated from the joint accelerations. The joint accelerations may be determined using the stored joint positions from previous iterations and the frequency at which the positions are calculated. The joint accelerations may be determined using stored joint velocities and the frequency at which the joint positions are calculated.

If the robot arm has more joints than are needed to achieve a desired wrist position, then the arm is said to have a redundancy. This means that there is more than one configuration of the arm joints which cause the wrist to have the desired wrist position. In this case, the arm controller determines a set of joint positions for the robot arm which cause the robot arm to have an optimal configuration. An optimal configuration may be defined by any one or combination of the following criteria:

- a configuration which avoids one or more arm joints being close to a joint limit.
- a configuration which avoids the surgical robot arm being close to a joint singularity. Certain poses of the surgical robot arm can become singular, meaning that it is impossible to make subsequent movements of the end effector in all directions with finite joint velocities.
- a configuration which avoids collisions with another object within the surgical robot arm's workspace.
- a configuration which is more desirable for the operating room staff. For example, the redundancy may enable the elbow portion 302 to adopt one or more positions for the same wrist position. One position of the elbow portion may be preferable over another to enable the bedside team to more easily access the patient's side.

Once the arm controller has determined all the joint positions of the remaining joints of the robot arm, it then moves on to step 904. At step 904, the arm controller sends control signals to the joint controllers to control the joint motors to drive the joints of the robot arm to the desired instrument drive joint positions and the determined joint positions for the remaining joints. The control signals sent by the arm controller to the joint controllers may include requested joint torques. Each joint controller converts the requested joint torque for a joint to a physical torque at that joint. The joint controller may implement this using closed loop current control of a brushless DC motor that is attached to it for driving the joint. The joint controller first determines the motor current to deliver the requested torque. This determination is done based on stored parameters relating to the motor type and gearbox of the joint. The joint controller also measures the current flowing in each phase of the motor which is used as an input to the closed loop torque control of the motor.

The control loop then returns to step 901, where the arm controller receives the next set of desired wrist position and desired instrument drive joint positions from the central controller.

In the above described control methods, the processing of the commands from the surgeon input device to drive signals for the joints of the surgical robot arm is distributed between the central controller and the arm controller.

The central controller determines the instrument drive joint positions and the position of the wrist. The configuration of the instrument and its length need to be known in order to determine the instrument drive joint positions and the wrist position. By distributing the processing as described herein the arm controller does not need to maintain details of the attached instrument. Thus, if an instrument was to be upgraded such that its dimensions or functionality change, or a new instrument was to be added to the system, a software upgrade would be required for the central controller only. This could be done via a download of the updated instrument data from a memory on the instrument itself. Alternatively, the updated instrument dimensions could be measured visually and input to the central controller. The arm controllers on all of the surgical robot arms of the system would not require a software upgrade. Thus, splitting up the control functions between the central controller and arm controller as described herein leads to a more efficient maintenance regime for the surgical robot system as a whole.

By distributing the processing as described herein, the arm controller performs fewer calculations, and thus consumes lower levels of processing power. This reduces the heat generated by the arm controller compared to if it was performing all the processing described herein. The temperature at which the surface of a surgical robot arm is permitted to reach during an operative procedure is strictly limited for safety reasons. Since the surgical robot arm is covered by a drape during a procedure for sterility reasons, the surface temperature of the arm increases as a result of the heat loss from the joint motors and other circuitry internal to the arm. By splitting up the control functions between the central controller and the arm controller as described herein, the arm controller is able to consume less processing power, and hence produce less heat loss, and thus reduce its contribution to heating up the surface of the arm.

The central controller is communicatively coupled to each robot arm in the surgical robotic system. The individual arm controllers are not communicatively coupled to each other. Thus, each arm controller has no knowledge of the position or even existence of any other robot arm in the system. By having the central controller determine the wrist position of each robot arm in the system, it can identify overlap of the workspace of two adjacent robot arms, and hence identify a potential collision between the two robot arms.

The arm controller has a high computational workload on other matters which include: driving the joints of the robot arm, receiving sensory data from the joint sensors, communicating with entities external to the robot arm, controlling application of power to the robot arm, fault detection in the robot arm. On the other hand, the central controller does not have a large computational workload. The central controller carrying out some of the calculations for the joint positions reduces the computational requirements of the arm controller, and hence enables the arm controller to dedicate processing power and hence speed to the other matters. Choosing to split the workload such that the central controller provides the arm controller with the wrist position and instrument drive joint positions means that the arm controller need only perform calculations in the robot arm's frame of reference. The arm controller does not need to perform any coordinate transformations. These are all performed by the central controller.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. An arm controller for a surgical robot arm, the surgical robot arm forming part of a surgical robotic system comprising a remote surgeon console, a central controller, the surgical robot arm and the arm controller, the surgical robot arm comprising a series of joints extending from a base to a terminal end for attaching to an articulated surgical instrument, the arm controller being co-located with the surgical robot arm and configured to:

determine a virtual pivot point, the virtual pivot point being located in a port through which the surgical instrument passes at all times when inside a patient's body;

transmit the virtual pivot point to the central controller;

receive sensory data and recalculate the virtual pivot point using the received sensory data; and transmit the recalculated virtual pivot point to the central controller.

2. The arm controller as claimed in claim 1, wherein the arm controller is configured to receive sensory data from one or more of:

sensors on the surgical robotic arm;

sensors on the instrument; and sensors on the port.

3. The arm controller as claimed in claim 1, wherein the arm controller is configured to periodically transmit the re-calculated virtual pivot point to the central controller during a surgical procedure.

4. The arm controller as claimed in claim 1, wherein the arm controller is configured to recalculate the virtual pivot point in response to the base of the surgical robot arm changing location.

5. The arm controller as claimed in claim 1, wherein the arm controller is configured to transmit an indication of the orientation of the surgical robot arm relative to the surrounding environment of the surgical robot arm to the central controller.

6. The arm controller as claimed in claim 5, wherein the surgical robot arm has an orientation interface manipulatable by an operator so as to identify an orientation of the robot arm relative to the surrounding environment of the robot arm and the arm controller is configured to receive the input indicating the orientation of the surgical robot arm relative to the surrounding environment from the orientation interface, and transmit this indication to the central controller.

7. The surgical robotic system of claim 1, the surgical robotic system comprising a second surgical robot arm, the second surgical robot arm comprising a series of joints extending from a base to a terminal end for attaching to a second articulated surgical instrument and a second arm controller, the series of joints including a wrist and a set of instrument drive joints which transfer drive from the surgical robot arm to joints of the second surgical instrument, wherein the central controller is remotely located from and communicatively coupled to the surgical robot arm and the second surgical robot arm.

8. The surgical robotic system as claimed in claim 7, wherein the second arm controller is configured to:

determine a virtual pivot point, the virtual pivot point being located in a port through which the second surgical instrument passes at all times when inside a patient's body;

transmit the virtual pivot point to the central controller;

receive sensory data and recalculate the virtual pivot point using the received sensory data; and transmit the recalculated virtual pivot point to the central controller.

9. A control system for a surgical robotic system, the surgical robotic system comprising a remote surgeon console and an articulated surgical robot arm comprising a series of joints extending from a base to a terminal end for attaching to an articulated surgical instrument, the series of joints including a wrist and a set of instrument drive joints which transfer drive from the surgical robot arm to joints of the surgical instrument, the control system comprising:

an arm controller of the surgical robot arm, the arm controller being co-located with the surgical robot arm; and a central controller communicatively coupled to and remotely located from the arm controller, the central controller also communicatively coupled to a surgeon input device of the surgeon console, the central controller configured to:

receive a virtual pivot point from the arm controller, the virtual pivot point being a position located in a port through which the surgical instrument passes at all times when inside a patient's body;

receive a command from the surgeon input device indicating a desired position of the distal end of the surgical instrument;

update one or more parameters stored at a parameter value store of the central controller based on the received command;

use the one or more parameters and the command from the surgeon input device to determine the desired position of the distal end of the surgical instrument;

use the received virtual pivot point and a known distance between the distal end of the surgical instrument and the wrist to transform the desired position of the distal end of the surgical instrument to a desired wrist position of the wrist of the surgical robot arm; and use the one or more parameters and the command from the surgeon input device to determine desired joint positions for the instrument drive joints.

10. A control system as claimed in claim 9, wherein the wrist of the surgical robot arm is located on the surgical robot arm where the rotation axes of a set of distal joints of the surgical robot arm intersect and/or the rotation axes of joints of the articulated surgical instrument intersect, the set of distal joints of the surgical robot arm being located distal to the base.

11. A control system as claimed in claim 10, wherein the set of distal joints consist of, in order, a roll joint, a pitch joint, a yaw joint, and a further roll joint.

12. A control system as claimed in claim 9, wherein the desired position of the articulated surgical instrument comprises a location of the distal end and an orientation of the distal end.

13. A control system as claimed in claim 9, wherein the surgical instrument is either:

a surgical endoscope; or configured to manipulate tissue, and the distal end of the surgical instrument is an end effector, and wherein the desired position of the articulated surgical instrument further comprises a spread of two end effector elements of the end effector.

14. The control system as claimed in claim 9, wherein determining the desired position of the distal end of the surgical instrument comprises:

determining a desired position of the distal end of the surgical instrument relative to a common ground frame of reference using the command from the surgeon input device and one or more of the stored parameters; and using orientation data to rotate the desired position of the distal end of the surgical instrument from the common ground frame of reference to the robot arm frame of reference, the orientation data indicating the orientation of the surgical robot arm relative to the surrounding environment of the surgical robot arm.

15. The control system as claimed in claim 14, wherein the central controller is configured to use the orientation data to transform the desired position of the distal end of the surgical instrument to the desired wrist position and to determine the desired instrument drive joint positions in the frame of reference of the surgical robot arm.

16. The control system as claimed in claim 9, wherein the central controller is configured to receive the orientation data from the arm controller.

17. The control system as claimed in claim 9, wherein the orientation data is predetermined and retrieved from the parameter value store of the central controller.

18. The surgical robotic system as claimed in claim 9, the surgical robotic system comprising a second surgical robot arm, the second surgical robot arm comprising a series of joints extending from a base to a terminal end for attaching to a second articulated surgical instrument and a second arm controller, the series of joints including a wrist and a set of instrument drive joints which transfer drive from the surgical robot arm to joints of the second surgical instrument, wherein the central controller is remotely located from and communicatively coupled to the surgical robot arm and the second surgical robot arm.

19. The surgical robotic system as claimed in claim 18, wherein the central controller is configured to:

receive a virtual pivot point from the second arm controller, the virtual pivot point being a position located in a port through which the second surgical instrument passes at all times when inside a patient's body;

receive a command from the surgeon input device indicating a desired position of the distal end of the second surgical instrument;

update one or more parameters stored at a parameter value store of the central controller based on the received command;

use the one or more parameters and the command from the surgeon input device to determine the desired position of the distal end of the second surgical instrument;

use the virtual pivot point received from the second arm controller and a known distance between the distal end of the second surgical instrument and the wrist to transform the desired position of the distal end of the second surgical instrument to a desired wrist position of the wrist of the second surgical robot arm; and use the determined wrist positions of the surgical robot arm and the second surgical robot arm to identify a potential collision between the two robot arms.

* * * * *